(12) United States Patent
McCabe et al.

(10) Patent No.: US 8,781,578 B2
(45) Date of Patent: Jul. 15, 2014

(54) MASS ATTRIBUTE DETECTION THROUGH PHRENIC STIMULATION

(75) Inventors: Aaron R. McCabe, Minneapolis, MN (US); Holly Rockweiler, Minneapolis, MN (US); Jacob I. Laughner, St. Louis, MO (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1266 days.

(21) Appl. No.: 12/616,336

(22) Filed: Nov. 11, 2009

(65) Prior Publication Data

US 2010/0125306 A1   May 20, 2010

Related U.S. Application Data

(60) Provisional application No. 61/114,542, filed on Nov. 14, 2008.

(51) Int. Cl.
*A61N 1/362* (2006.01)
*A61N 1/37* (2006.01)

(52) U.S. Cl.
CPC ................................ *A61N 1/3702* (2013.01)
USPC ............................................................. 607/9

(58) Field of Classification Search
USPC .................... 607/9, 17, 18, 62; 600/301, 587
See application file for complete search history.

(56) References Cited

U.S. PATENT DOCUMENTS

| 6,266,564 | B1 | 7/2001 | Hill et al. |
| 6,772,008 | B2 | 8/2004 | Zhu et al. |
| RE38,654 | E | 11/2004 | Hill et al. |
| 7,082,331 | B1 | 7/2006 | Park et al. |
| 7,245,971 | B2 | 7/2007 | Park et al. |
| 7,269,459 | B1 | 9/2007 | Koh |
| 7,277,757 | B2 | 10/2007 | Casavant et al. |
| 7,340,302 | B1 | 3/2008 | Falkenberg et al. |
| 7,340,306 | B2 | 3/2008 | Barrett et al. |
| 7,357,775 | B1 | 4/2008 | Koh |
| 7,363,085 | B1 | 4/2008 | Benser et al. |
| 7,363,086 | B1 | 4/2008 | Koh et al. |
| 7,421,296 | B1 | 9/2008 | Benser et al. |
| 7,424,321 | B2 | 9/2008 | Wariar et al. |
| 7,430,447 | B2 | 9/2008 | Min et al. |
| 7,704,211 | B1 * | 4/2010 | Koh ............................. 600/486 |
| 2006/0241711 | A1 | 10/2006 | Sathaye |
| 2007/0118054 | A1 * | 5/2007 | Pinhas et al. .................. 600/587 |

(Continued)

FOREIGN PATENT DOCUMENTS

WO    WO-2006/137067 A2    12/2006

OTHER PUBLICATIONS

"International Application Serial No. PCT/US2009/063975, International Search Report mailed Jan. 12, 2010", 4 pgs.

(Continued)

*Primary Examiner* — Christopher D Koharski
*Assistant Examiner* — Jeremiah Kimball
(74) *Attorney, Agent, or Firm* — Schwegman, Lundberg & Woessner, P.A.

(57) ABSTRACT

According to certain examples, an implanted medical device is used to determine a mass attribute of a patient. The patient's phrenic nerve is stimulated, and the diaphragmatic response is measured by an accelerometer. The measured response is analyzed in certain embodiments to determine a mass attribute. This information can help in the diagnosis of, and efficient response to, edema.

19 Claims, 3 Drawing Sheets

(56) References Cited

U.S. PATENT DOCUMENTS

| | | |
|---|---|---|
| 2008/0021504 A1 | 1/2008 | McCabe et al. |
| 2008/0188904 A1 | 8/2008 | Tehrani et al. |
| 2008/0234556 A1* | 9/2008 | Brooke et al. ............... 600/301 |
| 2008/0242976 A1 | 10/2008 | Robertson et al. |
| 2009/0024176 A1 | 1/2009 | Yun et al. |
| 2009/0062882 A1 | 3/2009 | Zhang et al. |
| 2009/0099621 A1 | 4/2009 | Lin et al. |
| 2010/0256462 A1* | 10/2010 | Rappaport et al. ............ 600/301 |

OTHER PUBLICATIONS

"International Application Serial No. PCT/US2009/063975, Written Opinion mailed Jan. 12, 2010", 8 pgs.

* cited by examiner

MASS ATTRIBUTE DETECTION THROUGH PHRENIC STIMULATION

CROSS-REFERENCE TO RELATED APPLICATION

This application claims the benefit of U.S. Provisional Application No. 61/114,542, filed on Nov. 14, 2008, under 35 U.S.C. §119(e), which is hereby incorporated by reference in its entirety.

BACKGROUND

Excess fluid buildup (edema) in a patient may be associated with many diseases. Edema results from inadequate or excessive response of homeostatic processes in the body. For example, acute pulmonary edema is a short-term fluid buildup in the lungs. In some people, such excess fluid buildup (also referred to as "decompensation") results from inadequate cardiac output of the heart, such as is associated with congestive heart failure (CHF). Pulmonary edema may occur late in the CHF disease process and may have serious consequences. The fluid accumulation in the lungs may result in labored breathing and, in severe cases, may even result in death. For these and other reasons, there is a need to detect edema.

OVERVIEW OF THE DISCLOSURE

Systems and methods are described that allow for improved monitoring and determination of edema by monitoring a patient's body mass in an ambulatory fashion. According to certain examples, an implanted medical device is used. The patient's phrenic nerve is stimulated, and the diaphragmatic response, similar to a 'hiccup,' is measured by an accelerometer. The measured response is analyzed in certain embodiments to determine a mass attribute. For example, a body mass can be estimated. An increasing body mass is one possible indicator of an edema, as an increase in the patient's overall mass can correspond to excess fluid buildup. Additional information can also be determined, including mass or fluid composition information. This information can help in the diagnosis of, and efficient response to, edema. Certain examples are described below.

Example 1 can include an implantable or other ambulatory accelerometer configured to sense an acceleration signal. The sensed acceleration signal is indicative of a response to a stimulation of a phrenic nerve of a patient. A processing circuit is in communication with the accelerometer and is configured to receive information from the acceleration signal. The processing circuit is further configured to determine a mass attribute of the patient based on the received information from the acceleration signal and to provide an indication of the mass attribute to a user or process.

In Example 2, the subject matter of Example 1 can optionally comprise a multi-axis accelerometer. The processing circuit can be configured to use information about a directional component of the acceleration signal sensed by the multi-axis accelerometer to determine the mass attribute of the patient.

In Example 3, the subject matter of any combination of Examples 1-2 can be configured to determine a thoracic mass of the patient.

In Example 4, the subject matter of any combination of Examples 1-3 can be configured to determine a systemic mass of the patient.

In Example 5, the subject matter of any combination of Examples 1-4 can be configured to determine an estimated composition of at least one of a body mass index, a fluid component level, a fatty tissue component level, or a lean tissue component level.

In Example 6, the subject matter of any combination of Examples 1-5 can optionally comprise a telemetry circuit operatively connected to the processing circuit and configured to wirelessly communicate information based on the mass attribute.

In Example 7, the subject matter of any combination of Examples 1-6 can optionally include an external computing interface comprising a display. The external interface can receive the information based on the mass attribute from the telemetry circuit and display an indication based on the mass attribute on the display.

In Example 8, the subject matter of any combination of Examples 1-7 can optionally include an implantable phrenic nerve stimulation circuit configured to provide the stimulation to the phrenic nerve of the patient.

In Example 9, the subject matter of any combination of Examples 1-8 can include at least a portion of the phrenic nerve stimulation circuit configured to be implanted in or on a heart of the patient.

Example 10 can include, or can be combined with the subject matter of any combination of Examples 1-9 to include receiving a signal indicative of a response in a patient to a stimulation of a phrenic nerve. A mass attribute of the patient is determined based at least in part on the received signal.

In Example 11, the subject matter of any combination of Examples 1-10 can optionally include determining an approximate composition of at least one of a body mass index, a fluid component level, a fatty tissue component level, or a lean tissue component level.

In Example 12, the subject matter of any combination of Examples 1-11 can optionally include measuring a peak-to-peak amplitude of the acceleration signal.

In Example 13, the subject matter of any combination of Examples 1-12 can optionally comprise determining a frequency response of the acceleration signal.

In Example 14, the subject matter of any combination of Examples 1-13 can optionally include using a multi-axis accelerometer. The mass attribute can be determined using a directional component of the sensed acceleration signal indicative of the response to the stimulation of the phrenic nerve.

In Example 15, the subject matter of any combination of Examples 1-14 can optionally include determining whether the mass attribute meets a specified criterion and generating an alert signal when the mass attribute meets the specified criterion.

In Example 16, the subject matter of any combination of Examples 1-15 can optionally include providing the stimulation of the phrenic nerve.

In Example 17, the subject matter of any combination of Examples 1-16 can optionally include providing the stimulation of the phrenic nerve using an electrode implanted in or on a heart of the patient.

In Example 18, the subject matter of any combination of Examples 1-17 can optionally include selecting a pacing vector, a pulse width, and a pulse amplitude sufficient to stimulate the phrenic nerve.

In Example 19, the subject matter of any combination of Examples 1-18 can optionally include timing the stimulation of the phrenic nerve to be provided at a specified portion of at least one of a cardiac cycle or a respiratory cycle.

In Example 20, the subject matter of any combination of Examples 1-19 can optionally include comparing the mass attribute to a systemic mass value.

In Example 21, the subject matter of any combination of Examples 1-20 can optionally include determining a systemic mass of the patient.

Example 22 can include, or can be combined with the subject matter of any combination of Examples 1-21 to include, a system comprising a means for receiving a signal indicative of a response in a patient to a stimulation of a phrenic nerve, and comprising a means for determining a mass attribute of the patient based at least in part on the received signal.

This overview is intended to provide an overview of subject matter of the present patent application. It is not intended to provide an exclusive or exhaustive explanation of the invention. The detailed description is included to provide further information about the present patent application.

DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

A patient's body mass is one possible indicator of an edema, as an increase in the patient's overall mass can correspond to excess fluid buildup. Monitoring a patient's body mass is typically done using a scale. According to certain examples described below, an implanted medical device (IMD) is used to determine a mass attribute of a patient in place of or in conjunction with other monitoring methods. These ambulatory weight monitoring systems can monitor the patient without the risk that the patient will forget or decline to check his or her weight at the prescribed times. In addition, the mass attribute measured by the IMD may be related more directly to an upper body mass, where the most dangerous excess fluid buildup commonly occurs. Additional information can also be determined, including mass or fluid composition information. This information can help in the diagnosis of, and efficient response to, edema.

Figure 1:
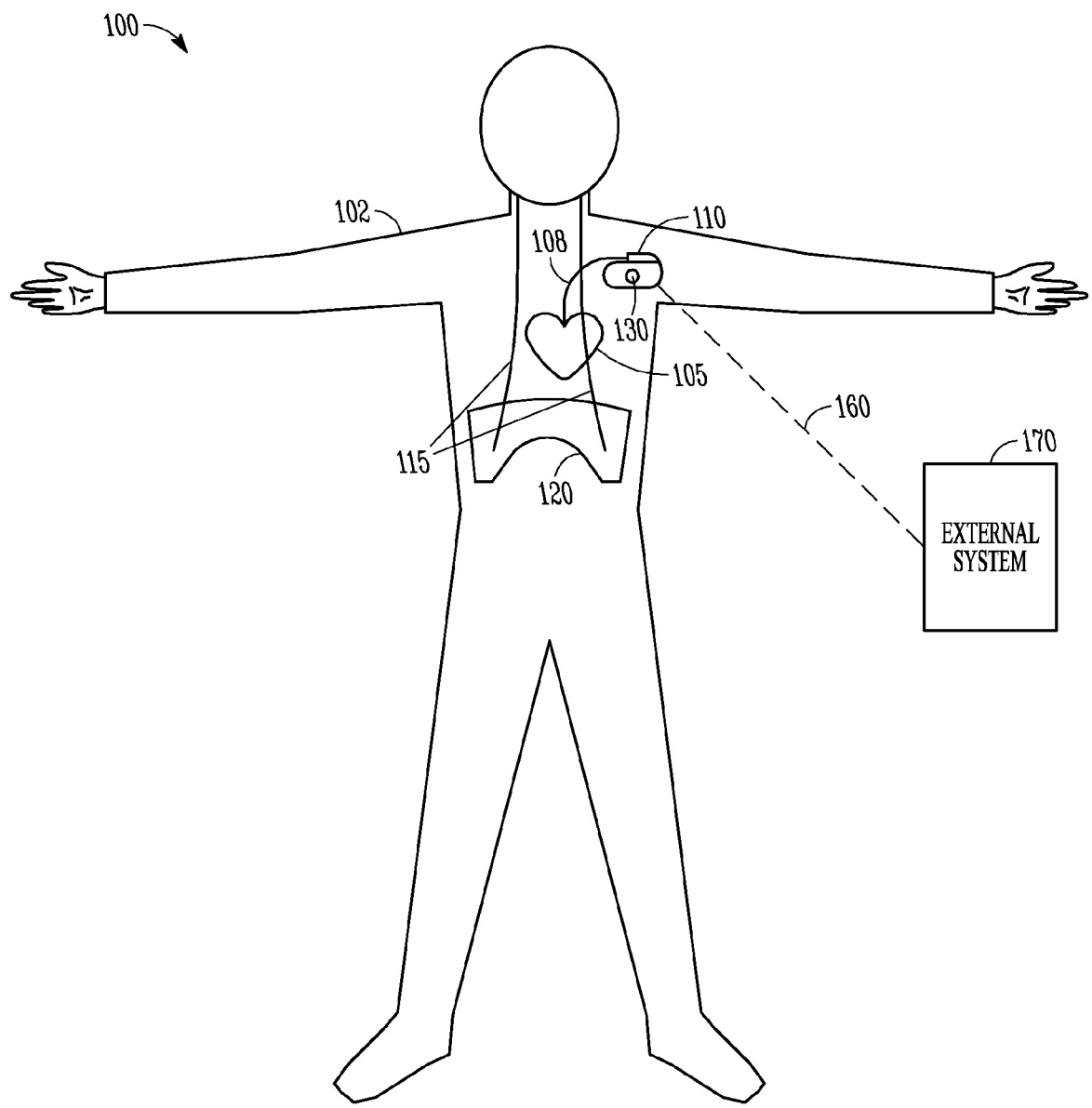
FIG. 1 shows an example of a system that uses an implantable medical device.

Certain embodiments of a system 100 that determines a patient mass attribute are illustrated in FIG. 1. The system 100 includes an IMD 110 and may be implemented with a system for treating a cardiac arrhythmia or otherwise improving heart function. Examples of the IMD 110 include, without limitation, an accelerometer, a pacer, a defibrillator, a cardiac resynchronization therapy (CRT) device, or a combination of such devices. The IMD 110 includes an accelerometer 130 that is used in certain examples described herein to detect information related to a mass attribute and to generate signals corresponding to that information. The IMD 110 is coupled by a cardiac lead 108 to a heart 105 of a patient 102 in the embodiments shown. In some examples, the IMD 110 does not provide therapeutic or diagnostic electrical stimulations or is not connected to the heart 105 via the cardiac lead 108. In the example shown, system 100 also includes an IMD programmer or other external system 170 that provides wireless communication signals 160 to communicate with the IMD 110, such as by using radio frequency (RF) or other telemetry signals.

The cardiac lead 108 includes a proximal end that is coupled to the IMD 110 and a distal end, coupled by an electrode or electrodes to one or more portions of a heart 105. In certain embodiments, one or more electrodes are located near the phrenic nerve 115. The phrenic nerve 115 controls contractions of the diaphragm 120 and the left branch runs proximate the left ventricle of the heart 105. A left ventricular lead may comprise an electrode configured to be implanted in the great cardiac vein of the heart 105 and near the phrenic nerve 115. Additional or alternative leads may be implanted in the patient 102, including leads having electrodes located outside the heart 102 or near the right branch of the phrenic nerve 115 in some embodiments.

The IMD 110 can provide an electrical stimulation via the electrodes of the implanted leads, the stimulation comprising a vector, pulse amplitude, and pulse width sufficient to stimulate the phrenic nerve 115. The electrodes can also deliver cardioversion defibrillation, pacing, resynchronization therapy, or combinations thereof to one or more chambers of the heart 105. In one example, the IMD provides therapeutic stimulation to the heart 105 via a first electrode or group of electrodes, and is configured to select a second electrode or group of electrodes to stimulate the phrenic nerve 115. The lead 108 can also be used for sensing electrical activity of a heart 105.

The IMD 110 includes components that are enclosed in a hermetically-sealed canister or "can." Additional electrodes may be located on the can, on an insulating header, or on other portions of the IMD 110 for providing unipolar pacing or defibrillation energy in conjunction with the electrodes located on or around heart 105.

The IMD 110 further comprises an accelerometer 130. The accelerometer 130 generates one or more electrical signals in response to movement, vibration, or strain. The accelerometer 130 may comprise a single-axis accelerometer, a multi-axis accelerometer, or several single-axis accelerometers. The movement detected by the accelerometer may comprise changes in the orientation or position of the patient 102, movement of the heart 105 corresponding to the cardiac cycle, movement corresponding to the respiratory cycle, vibrations corresponding to the contraction of the diaphragm, or the like.

Figure 2:
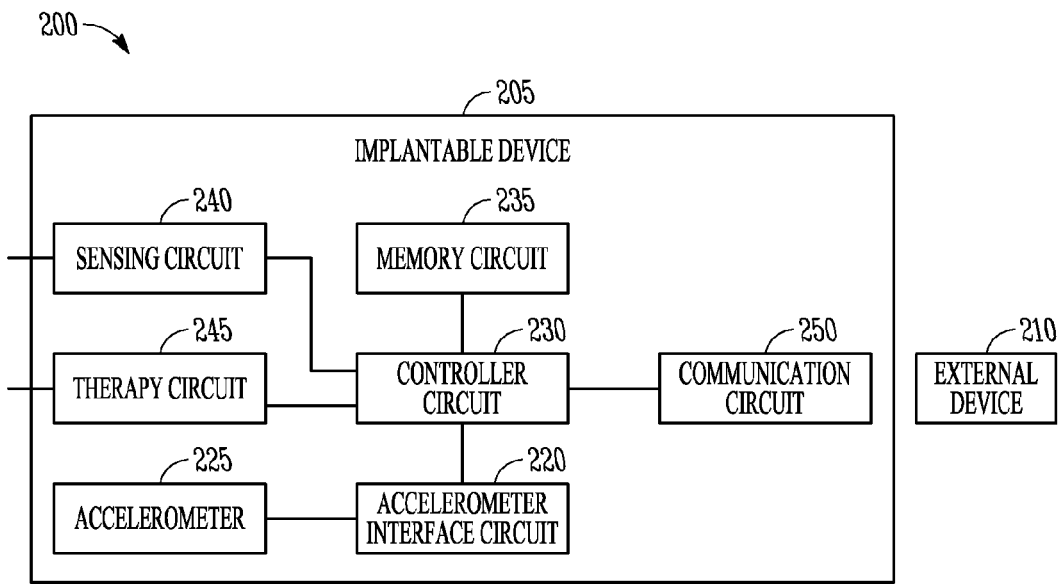
FIG. 2 shows an example of a system for determining a patient mass attribute.

A block diagram of portions of an example of a system 200 for determining a mass attribute of a patient are shown in FIG. 2. The system 200 includes an IMD 205 and an external device 210 operable to communicate with the IMD 205. The IMD 205 includes at least one accelerometer 225, an accelerometer interface circuit 220 coupled to the accelerometer 225, and a controller circuit 230 coupled to the accelerometer interface circuit 220.

The accelerometer 225 produces one or more electrical signals representative of the movement of the IMD 205, for example in response to a contraction of the diaphragm. The accelerometer 225 produces multiple electrical signals representative of non-parallel directional components of the movement of the IMD 205 in some embodiments. In an example, directional components correspond to orthogonal x-, y-, and z-axes, with the z-axis perpendicular to a patient's chest for a tri-axial accelerometer. In another example, the accelerometer 225 comprises a bi-axial accelerometer. A multi-axis accelerometer may be implemented as a single integrated device or as a combination of discrete devices, such as a combination of two or three single-axis devices. Certain devices that may be utilized to detect multi-axial acceleration signals are described in U.S. Pat. No. 7,424,321 issued to Wariar et al. on Sep. 9, 2008, entitled "Systems And Methods For Multi-Axis Cardiac Vibration Measurements," the entire contents of which are incorporated by reference.

In some examples, the acceleration interface circuit 220 includes signal processing circuitry corresponding to each of the directional components for processing the corresponding electrical signals. This allows signal processing such as frequency-selective filtering, gain-selective amplification, or selective sensing thresholds to be used on each of the one or more electronic signals. Filtering can allow for certain vibrations indicative of an induced contraction of the diaphragm to be separated from others such as breathing or muscle movement. Filtering can additionally isolate vibrations indicative of a response of certain tissue types such as fatty tissue, lean tissue, or fluids. Filtering and amplification can also improve the signal-to-noise ratio of the measurements. The accelerometer interface circuit 220 provides the signals representative of the movement of the system 200 to the controller circuit 230.

In some examples the controller circuit 230 includes a digital signal processor, application specific integrated circuit (ASIC), microprocessor, or other type of processor, interpreting or executing instructions in software or firmware. In some examples, the controller circuit 230 includes a state machine or sequencer that is implemented in hardware circuits.

The controller circuit 230 measures the one or more acceleration signals, including multiple directional components in some embodiments, to determine a mass attribute. The controller circuit 230 combines the multiple electrical signals together to produce an acceleration vector in some embodiments. Forming an acceleration vector adds directional information to the measurements. The directional information may be useful to discriminate other vibrations from a response to the contraction of the diaphragm. For example, cardiac vibrations may have a strong component along one axis such as the axis perpendicular to the patient's chest, while vibrations caused by a contraction of the diaphragm may have a strong component along another axis such as an axis corresponding generally to the patient's height. In one example, the controller circuit 230 measures the signals in relation to a physiological event, such as by synchronizing the measurement to a sensed or induced contraction of the diaphragm.

The IMD 205 also includes a memory circuit 235, a sensing circuit 240, and a therapy circuit 245 in the embodiments shown. The memory circuit 235 can store acceleration data, other measured or calculated data, or instructions for the operation of the IMD 205. The sensing circuit 240 is coupled to a cardiac lead or leads to sense one or more cardiac signals from a patient's heart in some embodiments. The controller circuit 230 can measure a diaphragmatic response in conjunction with a sensed cardiac signal. For example, a phrenic nerve stimulation pulse may be delivered and the response measured at a selected portion of the cardiac cycle. The cardiac signal may also be used with a filter to reduce signal noise corresponding to vibrations caused by the normal functioning of the heart. The therapy circuit 245 is attached to a cardiac lead or leads such as to provide cardioversion, defibrillation, pacing, resynchronization therapy, stimulation of the phrenic nerve, or one or more combinations thereof in some embodiments.

The IMD 205 further includes a communication circuit 250 for communicating wirelessly with the external device 210 using radio frequency (RF) or other telemetry signals. The IMD 205 communicates acceleration information or mass attribute data to the external device 210, as well as other data in some embodiments. In some examples, the controller circuit 230 is operable to communicate an indication of pulmonary edema or the like. The external device 210 may be a part of or in communication with a computer network such as a hospital computer network or the internet. The external device 210 may be wired to such a computer network or may communicate with the network wirelessly.

According to some embodiments, the external device 210 includes a display operable to display acceleration information in relation to a diaphragmatic response. In some embodiments, the external device is operable to display at least one representation of thoracic vibrations in multi-dimensional space. In some embodiments, the external device 210 is operable to display trending over time of a mass attribute determined from the acceleration signals. The trending information is useful to establish a trend indicative of the improving or worsening health condition of a patient. In some embodiments, the analyses are combined with one or more measurements of one or more other physiologic sensors to form a single decision as to whether to generate an alert. For example, trending of a mass attribute can be combined with trending of one or more other physiological measurements to form a decision whether to generate an alert if both are outside corresponding ranges. As an example, the trending of the mass attribute can be compared to the trending of a systemic mass value. These analyses can be done in the IMD 205, the external device 210, or both.

In some embodiments, the IMD 205 includes signal processing circuitry corresponding to each of the one or more electrical signals. In some embodiments, acceleration information is transmitted to the external device 210 and the external device 210 is operable to perform signal processing on the information and display the processed information. In some embodiments, the external device 210 is operable to perform noise rejection signal processing, such as frequency filtering or amplification, selectively for the information corresponding to each of the one or more electrical signals.

Figure 3:
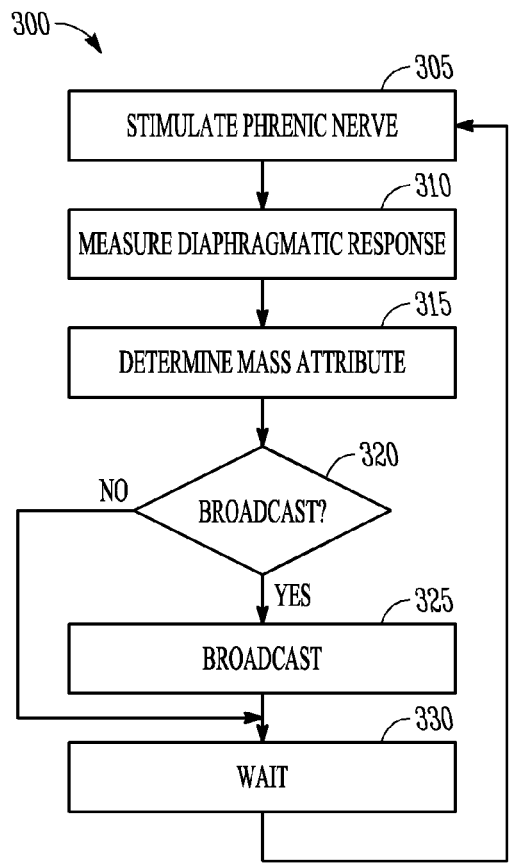
FIG. 3 shows an example of a method for determining a patient mass attribute.

Certain embodiments of a method 300 for monitoring a mass attribute of a patient are shown in FIG. 3. A mass attribute may comprise an upper body or thoracic mass, a body mass index (BMI) value, mass composition information, a systemic mass value, or the like. The mass attribute may be correlated to the existence of a pulmonary edema or other medical condition requiring medical attention, and monitoring the mass attribute may advantageously provide for the earlier and more accurate detection of the condition.

The method 300 may begin at the state 305 in the example shown. A stimulation or electric pulse is provided to the phrenic nerve at the state 305. The stimulation of the phrenic nerve may be provided, for example, by one or more electrodes of a lead system implanted in or on the heart. The electric pulse may additionally or alternatively be provided by one or more electrodes located outside the heart and near the phrenic nerve in some embodiments. In certain examples, an IMD determines a vector, a pulse width, and a pulse amplitude sufficient to stimulate the phrenic nerve and delivers a corresponding pulse via the appropriate electrodes. The electrodes used and the corresponding vector may be programmed into the IMD, or may be determined using an optimization technique based on detected responses to electrical pulses provided by various electrodes and sensors. A first set of electrodes can be used to provide therapeutic stimulation to a patient's heart, and the IMD can select a second set of electrodes to stimulate the phrenic nerve in some embodiments. For example, a right atrial lead can be used for pacing and a left ventricular lead can provide the phrenic nerve stimulation. A capture threshold can be determined for the selected electrodes corresponding to a pulse width and amplitude sufficient to reliably stimulate the phrenic nerve. An example of a method for determining a capture threshold for stimulation of the phrenic nerve is provided in U.S. Pat. No. 6,772,008 issued to Zhu et al. on Aug. 3, 2004, and entitled "Method And Apparatus For Avoidance Of Phrenic Nerve Stimulation During Cardiac Pacing," the entire contents of which are hereby incorporated by reference. While phrenic nerve stimulation is generally to be avoided in cardiac pacing to avoid unnecessary patient discomfort, similar capture threshold techniques can be used to configure the IMD to generate electrical pulses that can stimulate the phrenic nerve.

An electrical pulse sufficient to activate or stimulate the phrenic nerve may cause a sudden contraction of the diaphragm. The contraction of the diaphragm experienced by the patient may be similar to a 'hiccup.' At the state 310, that contraction and the resulting vibration of the upper body are measured. For example, the vibration of the upper body of the patient can be measured by an accelerometer contained in or operating in conjunction with an IMD. The accelerometer generates a current in response to and proportional to the movement, specifically the acceleration, of the device. The accelerometer may comprise a single-axis or multi-axis accelerometer, and can generate one or more signals. The signals contain directional specific information in some embodiments.

Figure 4:
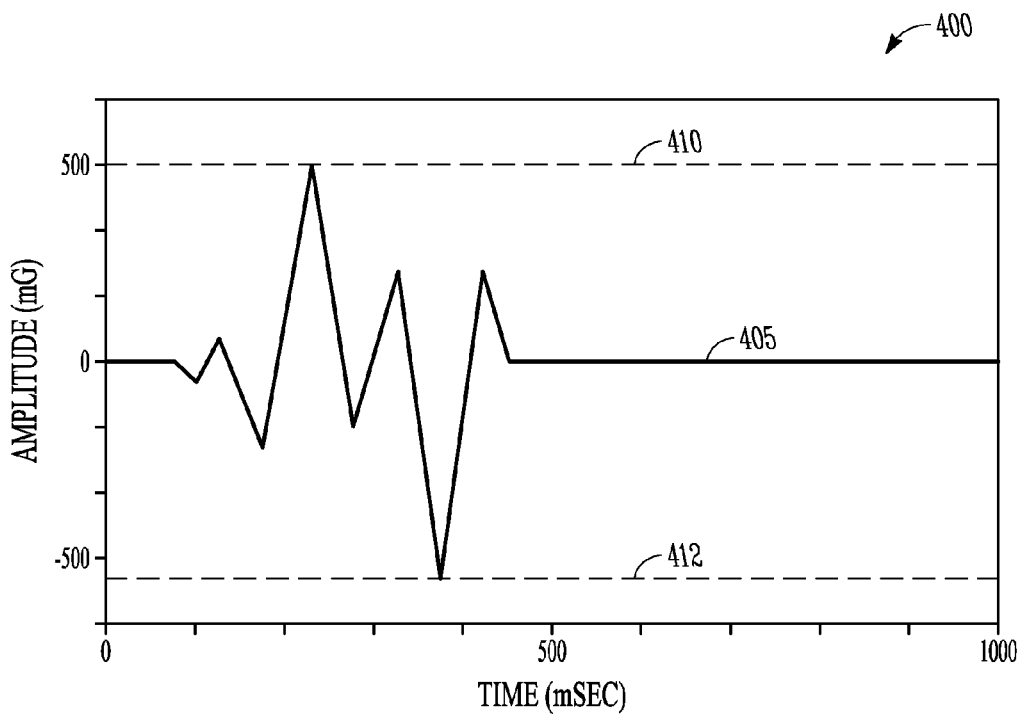
FIG. 4 shows an example of a plot of an acceleration signal used to determine a patient mass attribute.

FIG. 4 shows an example of a plot 400 corresponding to a signal 405 generated by an accelerometer during an induced contraction of the diaphragm. The plot 400 measures the amplitude of the detected acceleration signal 405 against time. The signal 405 can be measured constantly and analyzed at relevant times, or can be measured recurrently, such as at specified time intervals. In some examples, the signal is measured in response to an electrical pulse configured to stimulate the phrenic nerve and induce vibrations that are detected by the accelerometer. In the example shown, a pulse is provided at a time labeled as approximately 0 (zero) ms. Substantial vibrations are detected for about 500 ms after the contraction of the diaphragm. This time may vary based on the characteristics of the electrical pulse provided and the patient physiology. The intensity and direction of the vibrations also vary over this time, with a maximum detected amplitude 410 of approximately 500 mG and a minimum detected amplitude 412 of approximately −550 mG in the plot 400. The maximum amplitude 410 and the minimum amplitude 412 may correspond to the strongest detected vibrations in each of two opposite directions.

Measuring the diaphragmatic response at the state 310 is discussed above as occurring in response to a stimulation provided at the state 305. However, the state 310 can also act in response to a natural contraction of the diaphragm such as during a hiccup. For example, the vibrations caused by a natural contraction of the diaphragm can be differentiated from vibrations caused by general body movement or internal cycles, such as the cardiac or respiratory cycles, based on the magnitude and duration of the detected acceleration data. When the signal is determined to correspond to a contraction of the diaphragm, even when the contraction was not induced by an artificial electrical stimulation, the measured signal can be used to determine a mass attribute as described below.

Figure 5:
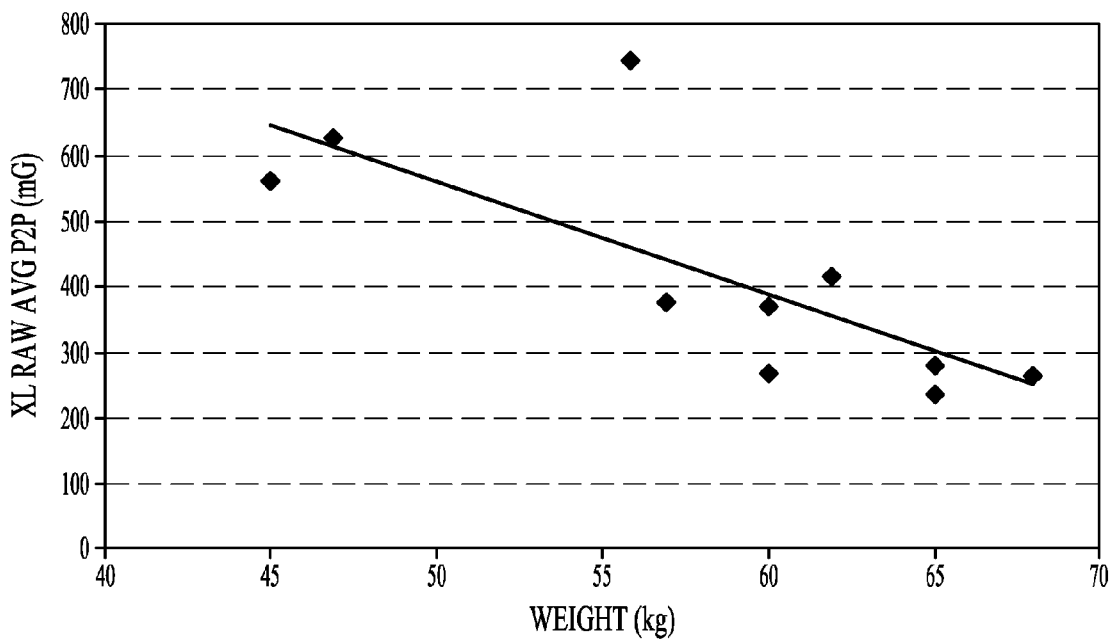
FIG. 5 shows a plot of experimental data.

At the state 315, the one or more signals measured by the accelerometer are analyzed to determine a mass attribute. For example, the peak-to-peak amplitude of the signal 400 between peaks 410 and 412 may be measured. The peak-to-peak amplitude has been found to be correlated to a systemic mass in an animal model. Experimental data showing the correlation between the peak-to-peak amplitude of a measured acceleration signal and the mass of animal test subjects is shown in FIG. 5. In FIG. 5, the maximum peak-to-peak amplitude detected in response to a stimulation of the phrenic nerve for ten animals is plotted against each animal's weight. As demonstrated by the experimental data and shown with a trend line, a larger peak-to-peak amplitude or maximum amplitude for a multi-dimensional vector corresponds generally to a lesser mass. The peak-to-peak amplitude is believed to also be correlated to an upper body mass. In another embodiment, a directional vector may be determined for the response detected by the accelerometer at times after the response, and a maximum magnitude may be used. Also with multiple directional acceleration signals, some directional components may be weighted differently than others in determining the mass attribute. The mass attribute can comprise an upper body mass value, such as 50 kg. In some embodiments, the mass attribute can comprise a value indicative of a change in the upper body or system mass relative to a stored value. For example, the mass attribute may comprise a ratio of the detected peak-to-peak amplitude to a stored amplitude.

In some embodiments the mass attribute can be determined by performing a frequency analysis of the one or more detected signals. For example, a frequency domain analysis of the measured response can indicate certain high energy frequencies or frequency bands. The high energy frequencies may correspond to signal components associated with a particular tissue type in the thoracic region of the patient. For example, a peak magnitude at a first characteristic frequency of fatty tissue may be used to approximate a fatty tissue component value. The fatty tissue component value may comprise a percentage value in some embodiments. Similar values can be determined for lean tissue and fluids. A BMI value may also be determined based on the component values. In some embodiments, any combination of any of the mass attributes discussed above can comprise the mass attribute.

At the decision state 320, it is determined whether an alert signal or some other signal should be broadcast by the IMD based on the determined mass attribute. A change in the mass attribute from an expected value or composition can trigger an alert in some embodiments. If the mass attribute indicates an increased upper body or thoracic mass an alert can be generated. In some embodiments, an alert is generated when the mass attribute falls outside a calculated range.

In some embodiments, the mass attribute is compared to a systemic mass value when determining whether to generate an alert. The systemic mass value can be stored by the IMD. The systemic mass value can be obtained, for example daily, from an external device such as a weight scale. An external programmer or ambulatory device can transmit the daily or an otherwise intermittent reading to the IMD, or the mass attribute can be transmitted to the external device and compared to the systemic mass attribute stored by the external device. When the systemic mass has increased by an amount indicating that the increase in the upper body mass is indicative of normal weight gain, then an alert is not generated or is modified in some embodiments.

In some examples, a signal indicative of the determined mass attribute is broadcast or not based on a device broadcast mode. For example, the IMD may be programmed to only broadcast when queried by an external device in a first mode. In another mode, the IMD may broadcast only when a dangerous condition is detected. In yet another mode, the IMD may broadcast any detected data including the determined mass characteristic and underlying signal data.

An alert as described above can comprise any signal indicative of the mass attribute or a condition of the mass attribute, such as being outside a safe or healthy range. In some embodiments, an alert signal includes information indicating a severity level. In some embodiments, an alert signal includes acceleration signal data. In some embodiments an alert signal may be configured to be broadcast with other data by the IMD.

If it is determined at the state 320 that an alert or signal is to be broadcast, then at the state 325 the signal is broadcast to an external device. The broadcast signal can include the alert as well as any other data to be transmitted by the IMD to the external device. The alert may be broadcast, for example, immediately after the mass attribute is detected and determined to be outside of a certain range, such as an increase in the measured upper body mass of approximately 2 kg. Alternatively, the mass attribute may be broadcast when an external device is determined to be within range, according to a specified schedule, or the like.

The broadcast alert can be displayed on the external device or another device networked to the external device. The alert for a dangerous condition can comprise a warning indicator including a textual warning, a visual warning, an audible warning, an electronic warning broadcast such as to a pager, or the like. The alert may additionally or alternatively be displayed as real-time or trended data on a display of the external device.

When an alert is broadcast at the state 325, or when it is determined at state 320 that no alert is broadcast, then the method 300 may continue to the state 330. At the state 330, the IMD may wait for further instructions, for a certain period of time, or for one or more conditions to be met before resuming the method 300 or some variation thereof. In an example, the IMD may return to the state 305 after a period of time such as one day or one week. The IMD may want to determine that the cardiac and respiratory cycles are both at a point in which stimulation of the phrenic nerve is not likely to cause damage to the patient, for example by interfering with the normal cardiac cycle. In another example, the method may return to the state 305 when instructed by an external device, such as a programmer or an ambulatory device in a patient's home in some embodiments. The IMD may be instructed to perform the method 300 or a variation thereof when an increase in systemic mass is detected. In some embodiments, the method 300 may proceed to state 310 when a natural contraction of the diaphragm is detected. The IMD may continue other operations, for example electrical measurement and stimulation of the heart, while waiting at the state 330.

The method above describes certain examples of steps that may be performed in order to determine and monitor a patient mass attribute. The methods described may be modified in other examples, such as by adding, removing, or substituting other states. For example, an electrical pulse may not be provided in some embodiments, and in other embodiments additional states may be provided for the storage of measured and analyzed data.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods.

The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Descrip-

What is claimed is:

1. A system comprising:
    an accelerometer configured to sense an acceleration signal indicative of a response to an electrical stimulation of a phrenic nerve of a patient;
    a processing circuit in communication with the accelerometer, the processing circuit configured to:
    receive information from the acceleration signal;
    determine a mass attribute of the patient using the received information from the acceleration signal, the determined mass attribute comprising at least one of a mass of an upper body of the patient, a mass of a thorax of the patient, a body mass index (BMI) value, mass composition information, and a systemic mass value of the entire patient; and
    provide an indication of the mass attribute to a user or process.

2. The system of claim 1, wherein the accelerometer comprises a multi-axis accelerometer, and wherein the processing circuit is configured to use information about a directional component of the acceleration signal sensed by the multi-axis accelerometer to determine the mass attribute of the patient.

3. The system of claim 1, wherein the processing circuit is configured to determine the mass composition information, the mass composition information comprising at least one of: a fluid component level, a fatty tissue component level, or a lean tissue component level.

4. The system of claim 1, comprising a telemetry circuit operatively connected to the processing circuit, the telemetry circuit configured to wirelessly communicate information based on the mass attribute.

5. The system of claim 4, further comprising an external computing interface comprising a display, wherein the external interface is configured to receive the information based on the mass attribute from the telemetry circuit and to display an indication based on the mass attribute on the display.

6. The system of claim 1, further comprising an implantable phrenic nerve stimulation circuit configured to provide the electrical stimulation to the phrenic nerve of the patient.

7. The system of claim 6, wherein the implantable phrenic nerve stimulation circuit is configured to be implanted in or on a heart of the patient.

8. A method performed by a medical device comprising:
    electrically stimulating a phrenic nerve of a patient;
    receiving an acceleration signal from an accelerometer, the acceleration signal indicative of a response in the patient to the electrical stimulation of the phrenic nerve;
    determining a mass attribute of the patient based at least in part on the received acceleration signal; the mass attribute comprising at least one of a mass of an upper body of the patient, a mass of a thorax of the patient, a body mass index (BMI) value, mass composition information, and a systemic mass value of the entire patient; and
    communicating an indication of the mass attribute to a user or process.

9. The method of claim 8, wherein determining the mass attribute comprises determining an approximate composition, wherein the approximate composition comprises at least one of: a fluid component level, a fatty tissue component level, or a lean tissue component level.

10. The method of claim 8, wherein determining the mass attribute comprises measuring a peak-to-peak amplitude of the acceleration signal.

11. The method of claim 8, wherein determining the mass attribute comprises determining a frequency response of the acceleration signal.

12. The method of claim 8, comprising sensing the acceleration signal, wherein sensing the acceleration signal comprises using a multi-axis accelerometer, and wherein determining the mass attribute comprises using a directional component of the sensed acceleration signal indicative of the response to the electrical stimulation of the phrenic nerve.

13. The method of claim 8, comprising:
    determining whether the mass attribute meets a specified criterion; and
    generating an alert signal when the mass attribute meets the specified criterion.

14. The method of claim 8, wherein electrically stimulating the phrenic nerve comprises using an electrode implanted in or on a heart of the patient.

15. The method of claim 14, further comprising selecting a pacing vector, a pulse width, and a pulse amplitude sufficient to electrically stimulate the phrenic nerve.

16. The method of claim 8, wherein electrically stimulating the phrenic nerve comprises timing the electrical stimulation of the phrenic nerve to be provided at a specified portion of at least one of a cardiac cycle or a respiratory cycle.

17. The method of claim 8, comprising comparing the mass attribute to the systemic mass value.

18. The method of claim 8, wherein determining the mass attribute comprises determining the systemic mass value of the patient.

19. A system comprising:
    means for electrically stimulating a phrenic nerve of a patient;
    means for receiving an acceleration from an accelerometer the acceleration signal indicative of a response in the patient to the electrical stimulation of the phrenic nerve;
    means for determining a mass attribute of the patient based at least in part on the received signal, the mass attribute comprising at least one of a mass of an upper body of the patient, a mass of a thorax of the patient, a body mass index (BMI) value, mass composition information, and a systemic mass value of the entire patient; and
    means for communicating an indication of the mass attribute to a user or process.

* * * * *